(12) United States Patent
Green et al.

(10) Patent No.: US 6,267,957 B1
(45) Date of Patent: Jul. 31, 2001

(54) ATTACHING AGENTS TO TISSUE WITH TRANSGLUTAMINASE AND A TRANSGLUTAMINASE SUBSTRATE

(76) Inventors: Howard Green, 82 Williston St., Brookline, MA (US) 02146; George D. Corey, 65 Harding St., Newton, MA (US) 02165; Bruce J. Compton, 30 Cottage St., Lexington, MA (US) 02173; Philippe Dijan, 170, rue de la Convention, 75015 Paris (FR)

(*) Notice: Subject to any disclaimer, the term of this patent is extended or adjusted under 35 U.S.C. 154(b) by 0 days.

(21) Appl. No.: 09/234,358

(22) Filed: Jan. 20, 1999

Related U.S. Application Data

(60) Provisional application No. 60/071,908, filed on Jan. 20, 1998.

(51) Int. Cl.⁷ ................ A61K 38/45; A61K 38/48; A61K 38/00; C12N 11/02; C07K 17/02
(52) U.S. Cl. .................. 424/94.5; 424/59; 424/94.63; 424/401; 435/16; 435/177; 435/193; 514/2; 530/402; 530/812
(58) Field of Search ............... 435/16, 174, 177, 435/193; 424/94.63, 94.5, 401, 59; 514/2; 530/402, 812

(56) References Cited

U.S. PATENT DOCUMENTS

| | | | |
|---|---|---|---|
| 4,279,996 | 7/1981 | Yoshioka et al. | 435/69 |
| 4,338,214 | 7/1982 | Fischer et al. | 252/545 |
| 4,369,037 | 1/1983 | Matsunaga et al. | 8/127.51 |
| 4,517,175 | 5/1985 | Iwabuchi et al. | 424/70 |
| 4,699,778 | 10/1987 | Marty | 424/59 |
| 4,705,682 | 11/1987 | Moeller et al. | 525/70 |
| 4,726,942 | 2/1988 | Lang et al. | 424/47 |
| 4,832,946 | 5/1989 | Green | 424/70 |
| 4,839,168 | 6/1989 | Abe et al. | 424/74 |
| 4,879,116 | 11/1989 | Fox et al. | 424/682 |
| 4,885,169 | 12/1989 | Gazzani | 424/104 |
| 4,973,473 | 11/1990 | Schneider et al. | 424/63 |
| 5,075,019 | 12/1991 | Evans et al. | 252/34 |
| 5,080,888 | 1/1992 | Grollier et al. | 424/61 |
| 5,091,173 | 2/1992 | Buultjens et al. | 424/70 |
| 5,100,956 | 3/1992 | O'Lenick, Jr. | 514/54.1 |
| 5,135,913 | 8/1992 | Pickart | 424/16 |
| 5,156,956 | 10/1992 | Motoki et al. | 425/68.1 |
| 5,490,980 | 2/1996 | Richardson et al. | 424/94.6 |
| 5,525,336 | 6/1996 | Green et al. | 424/94.5 |
| 5,773,577 | 6/1998 | Cappello | 530/350 |

FOREIGN PATENT DOCUMENTS

| | | |
|---|---|---|
| 13742 | 9/1988 | (AU). |
| 19647863A | 5/1998 | (DE). |
| 0285 474 | 10/1988 | (EP). |
| 0481 504 | 10/1991 | (EP). |
| 0511 116 | 10/1992 | (EP). |
| 0704221A | 3/1996 | (EP). |
| 0615 745 | 5/1997 | (EP). |
| 2659352 | 9/1991 | (FR). |
| 61-172807 | 8/1986 | (JP). |
| 02169511 | 6/1990 | (JP). |
| 2-204407 | 8/1990 | (JP). |
| 03038511 | 2/1991 | (JP). |
| 03083908 | 4/1991 | (JP). |
| 5-56785 | 3/1993 | (JP). |
| 05085924 | 4/1993 | (JP). |
| WO95/24929 | 9/1955 | (WO). |
| WO92/12238 | 7/1992 | (WO). |
| WO 94/18945 | 9/1994 | (WO). |
| WO94/23738 | 10/1994 | (WO). |
| WOUS96/11990 | 4/1996 | (WO). |
| WO 98/13381 | 4/1998 | (WO). |

OTHER PUBLICATIONS

Rice, "The Cornified Envelope of Terminally Differentiated Human Epidermal Keratinocytes Consists of Cross–Linked Protein", *Cell*, 11:417–422 (1977).

Simon, "Enzymatic Cross–Linking of Involucrin and Other Proteins by Keratinocyte Particulates in Vitro," *Cell*, 40:677–683 (1985).

Steven, "Biosynthetic Pathways of Filaggrin and Loricrin—Two Major Proteins Expressed by Terminally Differentiated Epidermal Keratinocytes," *J. of Structural Biology*, 104:150–162 (1990).

Highley, "The Epidermal Keratinization Process," *Cosmetics & Toiletries*, 99:57–62 (1984).

Rialdi et al., l"Filaggrin Overview; Functions and Cosmetic Aim," *Cosmetics & Toiletries*, 103:89–94 (1988).

(List continued on next page.)

*Primary Examiner*—David M. Naff
(74) *Attorney, Agent, or Firm*—Wolf, Greenfield & Sacks, P.C.

(57) ABSTRACT

Methods, products and kits are provided for attaching agents to tissue with a linking molecule in the presence of transglutaminase. The linking molecule and/or agent is a substrate of transglutaminase. The agent can be a nonprotein or an enzyme such as cholinesterase or phosphodiesterase. The transglutaminase may be exogenously added or be endogenous in tissue. In specific embodiments, the linking molecule contains at least two contiguous linked glutamines or at least three contiguous linked lysines. A conjugate of the agent and the linking molecule may be applied to tissue, and in the presence of transglutaminase covalently bonded to the tissue via the linking molecule. A complementary linking molecule rich in lysines may be first attached to the tissue in the presence of transglutaminase, and then covalently bonded to a glutamine-containing linking molecule of the conjugate in the presence of transglutaminase. In another embodiment, a linking molecule containing multiple glutamines is covalently bonded to tissue in the presence of transglutaminase, and an agent containing multiple lysines is covalently bonded to the linking molecule in the presence of transglutaminase. Alternatively, the linking molecule contains multiple lysines and the agent contains multiple glutamines. Two tissues can be sealed together by holding the tissues in contact with each other in the presence of transglutaminase.

48 Claims, 2 Drawing Sheets

OTHER PUBLICATIONS (Abstract) *Women's Wear Daily*, p. 6 (Oct. 9, 1992).

Banks–Schlegal, "Involucrin Synthesis and Tissue Assembly by Keratinocytes in Natural and Cultured Human Epithelia," *J. of Cell Biology*, 90:732, 737 (1981).

Eckert, "Structure and Evolution of the Human Involucrin Gene," *Cell*, 46:583–589 (1986).

Etoh, "Involucrin Acts as a Transglutaminase Substrate at Multiple Sites," *Biochemical and Biophysical Research Communications*, 136:51–56 (1986).

Fietz, "The cDNA–deduced Amino Acid Sequence for Trichohyalin, A Differentiation Marker in the Hair Follicle, Contains a 23 Amino Acid Repeat," *J. of Cell Biology*, 110:427–436 (1990).

Steven, M. et al., "Protein Composition of Cornified Cell Envelopes of Epidermal Keratinocytes," *J. Cell Science*, 107:693–700 (1994).

Folk, "Transglutaminase (Guinea Pig Liver)," in *Methods in Enzymology*, vol. 17A, 1970, p. 889–894, Tabor H. and C. Tabor, Eds.

Green, "Terminal Differentiation of Cultured Human Epidermal Cells," *Cell*, 11:405–416 (1977).

Greenberg, "Transglutaminases: Multifunctional Cross–linking Enzymes that Stabilize Tissues," *FASEB J.*, 5:3071–3077 (1991).

Hohl, "Cornified Cell Envelope," *Dermatologica*, 180:201–211 (1990).

Hohl, "Characterization of Human Loricrin," *J. of Biological Chemistry*, 266:6626–6636 (1991).

Kvedar, "Characterization of Sciellin, a Precursor to the Cornified Envelope of Human Keratinocytes," *Differentiation*, 49:195–204 (1992).

Markova, Profilaggrin Is a Major Epiderman Calcium–Binding Protein, *Molecular and Cellular Biology*, 13:613–625 (1993).

Marvin, "Cornifin, a Cross–Linked Envelope Precursor in Keratinocytes that Is Down–Regulated by Retinoids," *Biochemistry*, 89:11029–11030 (1992).

Mehrel, "Identification of a Major Keratinocyte Cell Envelope Protein, Loricrin," *Cell*, 61:1103–1112 (1990).

Phillips, "Primary Structure of Keratinocyte Transglutaminase," *Biochemistry*, 87:9333–9337 (1990).

Rice, "Presence in Human Epidermal Cells of a Soluble Protein Precursor of the Cross–Linked Envelope: Activation of the Cross–Linking by Calcium Ions," *Cell*, 18:681–694 (1979).

International Search Report: PCT/US99/01193 (related PCT Case—WO).

Davies, et al., *Adv. Exp. Med. Biol.* 250, 391–401 (1988).

Pober, J.S., et al., *Biochemistry*, vol. 17, No. 11:2163–2169 (1978).

Lajemi, M., et al., *Histochemical Journal* 29:593–606 (1997).

Kahlem, et al., *Proc. Natl. Acad. Sci., USA*, vol. 93, pp.14580–14585 (Dec., 1996)(Appendix A).

ATTACHING AGENTS TO TISSUE WITH TRANSGLUTAMINASE AND A TRANSGLUTAMINASE SUBSTRATE

This application claim benefit to provisional application Ser. No. 60/071,908 Jan. 20, 1998.

FIELD OF THE INVENTION

This invention relates to the linkage of agents to tissue by transglutaminase and involves methods, products and kits relating thereto.

BACKGROUND OF THE INVENTION

Transglutaminases are a family of calcium-dependent enzymes mediating covalent cross-linking reactions between specific peptide bound (4-glutamyl residues and various primary amino groups of peptide-bound lysines or polyamines, acting as amine donor substrates (Davies, et al., Adv. Exp. Med. Biol. 250, 391–401, 1988). These enzymes stabilize biological structures via the formation of isopeptide cross-links. In mammals, at least five enzymatically active transglutaminases have been identified, cloned and sequenced. The number of proteins acting as glutaminyl substrates for transglutaminases is restricted, and no obvious consensus sequence around these substrates' glutamines has been found.

Three main lines of investigation have been conducted surrounding transglutaminases. These enzymes have been used to label membrane proteins and, in the absence of exogenous amines, to catalyze the formation of (4-glutamyl)-lysyl cross-links between them. The labeling is quite specific and can be carried out under mild (physiological) reaction conditions. Thus, for example, transglutaminases were used to study rhodopsin in the intact disc membrane, as only residues of rhodopsin located in the aqueous phase in the exposed side of the disc membranes were expected to be labeled. In these experiments, rhodopsin was labeled by transglutaminase using putrescine and dansylcadaverine as detectable substrates.

The role of transglutaminases in living cells also has been studied, for example, using the cell-penetrating labeled substrate fluoresceincadaverine for detecting amine acceptor protein substrates accessible to active transglutaminase in living cells. A similar strategy was employed using 5-(biotinamido)-pentylamine as a label. Such labeled substrates can be detected directly, for example by fluorescence, or can be detected indirectly, for example using antibodies, to identify native proteins to which the labeled substrate has been covalently attached by transglutaminase. See, Pober, J. S. et al., Biochemistry, Vol. 17, No. 11:2163–2169 (1978); Lajemi, M. et al., Histochemical Journal 29:593–606 (1997).

More recently, an investigation was carried out to determine if polyglutamine is a transglutaminase substrate. It was determined that as long as polypeptides including stretches of polyglutamine are rendered sufficiently soluble by the flanking residues, all were excellent substrates of transglutaminase. Based upon these studies, it was speculated that certain diseases such as Spinocerebellar ataxia Type I, Machado-Joseph disease, and Dentato-Rubral pallidoluysian atrophy which are characterized by proteins having polyglutamine stretches, may arise as a result of aggregation of such proteins acted upon by a transglutaminase.

It also is described in U.S. Pat. No. 5,525,336 (the disclosure of which is incorporated herein by reference in its entirety) that transglutaminases and corneocyte proteins, the natural substrates of transglutaminases, can be used together as cosmetic treatments to cross-link preparations of corneocyte proteins to the outer layer of skin, hair or nails to form a protective layer on the skin, hair or nails.

U.S. Pat. No. 5,490,980 describes selecting agents having or modifying agents to have an aliphatic amine, and then attaching those agents to skin, hair or nails using transglutaminase. While the idea was sound in principle, in practice the '980 applicants achieved results that were barely above background. (See Example Section of '980 patent). An aliphatic amine was applied in the examples as a single linking molecule or prophetically in clusters (according to a formula in the '980 patent). In selecting the amine moiety of the pair of known transglutaminase substrate moieties, the '980 patent taught away from using the carboxamide substrate moiety.

SUMMARY OF THE INVENTION

It has been discovered, surprisingly, that certain substrates of transglutaminase are particularly desirable for use as linking molecules to attach agents to proteinaceous material such as body tissue. It also has been discovered that molecules, including native peptides and conjugates according to the invention, can be screened to determine those that can be substrates of transglutaminases, and then such molecules can be attached to body tissue. Method of attaching agents to body tissue and methods of screening molecules using transglutaminase are provided. In addition, compositions of matter suitable as substrates for transglutaminase and kits containing such molecules together with transglutaminase are provided.

According to one aspect of the invention, a method is provided for attaching a non-corneocyte protein, non-labeling agent to a body tissue. A conjugate of the agent and a linking molecule having a carboxamide, the linking molecule being a carboxamide-bearing substrate of transglutaninase, is applied to the body tissue. Transglutaminase also is applied to the body tissue, in an amount effective for cross-linking the conjugate to the body tissue via the linking molecule. The cross-linking then is allowed to occur. In certain embodiments the agent is not fibronectin (i.e., a nonfibronectin agent). In certain embodiments the agent is not an extracellular matrix protein (i.e. a non-extracellular protein agent). Preferably the linking molecule comprises a polymer of at least 3, 4 or 5 linked units, each unit being a carboxamide substrate of transglutaminase.

According to another aspect of the invention, a method is provided for attaching a non-corneocyte protein, non-labeling agent to a body tissue. The method involves selecting a non-corneocyte protein, non-labeling agent that is a carboxamide substrate for transglutaminase. The agent, in an isolated form, then is applied to the body tissue in the presence of a sufficient amount of transglutaminase to cross-link the isolated agent to the body tissue. The cross-linking then is allowed to occur. In this embodiment, the agent can be a conjugate of a native, non-corneocyte, non-labeling active agent and a linking molecule not native to the agent. It also is the case that the agent can be a native agent free of conjugation with groups not native to the agent. The agent in certain embodiments is a non-extracellular matrix protein agent.

In either of the foregoing embodiments, the linking molecule can be any number of a variety of molecules. In some embodiments, the linking molecule is at least one glutamine. The linking molecule, likewise, can be one bearing multiple reactive carboxamides, such as two or more contiguous linked L or D glutamines. D glutamines have the advantage of being physiologically more stable than L glutamines. In a preferred embodiment, the linking molecule is a polymer rich in carboxamides that are substrates of transglutaminase, such as a polymer rich in glutamine. The linking molecule also can be a polymer rich in both carboxamides and aliphatic amines, such as one rich in both glutamine and lysine. A polymer rich in glutamine, lysine, or glutamine and lysine is a molecule wherein at least 20% of the units of the polymer are glutamine, lysine or glutamine and lysine, respectively or wherein the molecule includes at least three, preferably four and most preferably five contiguous, linked transglutamines substrates, preferably linked by peptide bonds. A polymer rich in glutamines, lysines or glutamines and lysines, can be a polymer that contains at least 30% glutamines, lysines or glutamines and lysines, at least 40% glutamines, lysines or glutamines and lysines, or even 50% or more glutamines, or glutamines and lysines.

In certain preferred embodiments, the methods described above involve first preparing the body tissue for the attachment of the agent to the body tissue. In one important embodiment, a separate "complementary" linking molecule that is attachable to the linking molecule by transglutaminase is first attached to the body tissue to provide multiple, accessible linking sites for the attachment of the linking molecule to the body tissue. As used herein a pair of molecules which are covalently joined by transglutaminase are said to be complementary molecules. The complementary linking molecule can be attached to the body tissue by any suitable means, but preferably is attached by applying the complementary linking molecule to the body tissue, and applying transglutaminase to the body tissue in an amount effective for cross-linking the complementary linking molecule to the body tissue. Cross-linking then is allowed to occur. Preferably, the complementary linking molecule is a polymer rich in lysine, glutamine, or both glutamine and lysine.

Layers of such linking molecules can be attached to body tissue. To exemplify, polyglutamine could first be attached to the surface of a body tissue using transglutaminase. Then, polylysine could be attached to the polyglutamine using transglutaminase. Subsequently polyglutamine could be attached to the polylysine by transglutaminase, and so forth, to create by amplification alternating layers of such molecules on the body tissues, for example, for bulking purposes or to provide an even, continuous bed of reactive groups for linking an active agent to the body tissue.

For example, polymers comprising polyglutamine may first be attached to a body tissue as primary linking molecules. Then, polymers comprising the complementary linker (e.g. polylysine) can be attached to the body tissue via the polymers comprising polyglutamine. Finally, agents conjugated with polyglutamine then may be applied to the coated body surface and easily attached to the exposed amines of the polylysines.

In important embodiments, the native agent is not itself a substrate of transglutaminase. Thus, it is required that the agent be conjugated to a substrate of transglutaminase whereby the agent may be attached to the body tissue by such a substrate which acts as the linking group. It also is possible to modify peptide agents by adding a side group, whereby the agent which itself is not a substrate of transglutaminase is converted to a substrate of transglutaminase.

According to the foregoing methods, the agents and conjugates are attached to proteinaceous material. The preferred proteinaceous material is body tissue, including the integument, a wound bed, internal organs or internal tissue of a living subject.

According to the foregoing methods, the agent can be any variety of agents, including cosmetics such as bulking agents and coloring agents, sunscreen agents, enzymes including cholinesterase and phosphodiesterase, pharmaceutical agents, ligands of ligand-receptor complexes, receptors of ligand-receptor complexes and the like. In one important embodiment, the agent is a member of a noncovalent coupling pair, such as biotin and avidin, to provide a universal linker as discussed in greater detail below. In certain embodiments, particularly those employing pharmaceutical agents, the bond between the agent and the linking molecule can be a bond which cleaves under normal physiological conditions or which can be caused to cleave specifically, for example, by light. In many instances where the agent is not itself a substrate of transglutaminase, the agent is a nonprotein.

According to another aspect of the invention, a method is provided for attaching an agent to a body tissue. A linking molecule, that is covalently bonded to the agent in the presence of transglutaminase, is attached to the body tissue. Then, an agent that is a substrate of transglutaminase is applied to the body tissue. Transglutaminase also is applied to the body tissue, in an amount effective to cross-link the agent to the linking molecule. Cross-linking then is allowed to occur. The linking molecule can be attached to the body tissue by any suitable means, but preferably is itself a substrate of transglutaminase and preferably is attached to the body tissue by applying the linking molecule to the body tissue together with transglutaminase, the transglutarminase being present in an amount effective to cross-link the linking molecule to the body tissue. Preferred agents and linkers are as discussed above. Most preferred linking molecules are glutamine, lysine and polymers of glutamine and/or lysine or polymers that are rich in glutarnine, or lysine, or both glutamine and lysine.

In this embodiment, the agent can be any substance including those listed above (with or without conjugated complementary linking molecules depending on whether the agent is itself a substrate of transglutaminase) but also including visible labels, extracellular matrix proteins and corneocyte proteins. Preferred body tissues are as described above. The transglutaminase may be endogenous transglutaminase.

According to another aspect of the invention, a method is provided for attaching an agent to a body tissue. The method involves first attaching to the body tissue a linking molecule which is covalently bondable to the agent in the presence of transglutaminase. Then, the method involves applying to the body tissue having the linking molecule attached thereto an agent that is a substrate of transglutaminase and that is covalently bondable to the linking molecule in the presence of transglutaminases, the applying carried out in the presence of the sufficient amount of transglutaminase effective to cross-link the agent to the cross-linking molecule. Cross-linking then is allowed to occur. Preferred agents, linking molecules and body tissues are as described above.

According to another aspect of the invention, a method for attaching a nonextracellular matrix protein, preferably nonlabeling, agent to a body tissue is provided. The method involves applying to the body tissue a conjugate of the agent and a linking molecule, the linking molecule being a polymer carrying at least 3 aliphatic amines spaced along the polymer, applying to the body tissue transglutaminase in an amount effective for crosslinking the linking molecule to the body tissue, and allowing crosslinking to occur. The aliphatic amines can be the side chain of L or D lysines. D lysines have the advantage of being physiologically more stable than L lysines. Most preferably, the linking molecule is selected from the group consisting of at least 3, at least 4 and at least 5 contiguous lysines attached to one another directly by peptide bonds. The polymer also can be one rich in aliphatic amines such as one rich in lysines, as described above. Preferred agents and body tissues are as described above.

According to another aspect of the invention, compositions of matter are provided. The compositions include conjugates of a non-corneocyte, non-labeling agent and a linking molecule having a carboxamide, the linking molecule being a carboxamide bearing substrate of transglutaminase, wherein the agent is selected from the group consisting of a sunscreen agent, a cosmetic, an enzyme, a coloring agent, a pharmaceutical agent, a member of a ligand/receptor pair, a component of a high-affinity non-covalent coupling pair, a tissue sealant, an insecticide, an insect repellant, a bactericide, a fungicide, and the like. The linking group is not native to the agent. Preferred linking molecules are as described above. In certain embodiments, particularly those involving the pharmaceutical agents, the bond between the agent and the linking group or molecule is a hydrolyzable bond or light cleavable bond. In certain important embodiments, the agent is a non-protein. In other important embodiments, the agent is an active agent. In other important embodiments, the agent, in its native form free of conjugation to the linking molecule, is not itself a substrate of transglutaminase.

Another composition is as described above, except that the linking molecule is one bearing multiple, spaced aliphatic amines. Such linking molecules carry at least three, preferably at least 4 and more preferably, at least 5 aliphatic amines that are substrates of transglutaminase, attached to the backbone of the linking molecule and separated from one another and spaced at discrete intervals. The linking molecule can be a polymer, and, in one important embodiment has at least 3, 4 or 5 contiguous lysines attached directly to one another by peptide bonds. In another embodiment the polymer is rich in aliphatic amines.

According to other aspects of the invention, kits are provided. One such kit includes a package housing a first container containing a composition of matter as described above and a second container containing transglutaminase. The kit can further comprise a third container housed by the package, the third container containing a linking molecule that is a substrate of transglutaminase and that is covalently bondable, in the presence of transglutaminase, to the composition contained in the first container. The various containers also can contain vehicles, preservatives, buffers, calcium chelators and calcium (which is necessary for the activity of transglutaminase).

As mentioned above, the tissue can be pretreated to make it more receptive to the action of transglutaminase. In one embodiment described above, this is accomplished by attaching polymers rich in glutamine, lysine or both glutamine and lysine to the body tissue. In other embodiments, the tissue is treated to expose reactive glutamines and/or lysines by washing, chemical treatment, etc. Detergents and lipases can be used to remove fatty acids and oils. Roughening agents such as pumice, silica and sandpaper can be employed to remove dead tissue and other obstructions, and chemical agents such as sodium hydroxide can be used to expose reactive groups. Combinations of the foregoing are contemplated.

The invention also involves the use of transglutaminase to 'glue' two tissues together. Two tissues are held under force in contact with one another in the presence of an effective amount of transglutaminase, whereby the transglutaminase causes the cross-linking of the tissue to occur. Preferably, the surfaces of the tissues to be glued to one another are treated with a substrate of transglutaminase such as polymers rich in glutamine, lysine or both glutamine and lysine to create highly reactive surfaces in the presence of transglutaminase. These highly reactive surfaces are bonded to one another. Even more preferably, the surfaces of the tissue are first treated with a linking molecule to crosslink the linking molecule to the surfaces, then a linking molecule complementary to the first is applied to crosslink the linking molecules to one another and glue the tissue. The transglutaminase may be exogenously supplied. The tissue may be held together by any conventional means, such as sutures, tape, stapes and the like.

The agent also can be in a vehicle such as a microparticle, e.g. a microsphere or a nanosphere, the microsphere or nanosphere being rich in carboxamide or aliphatic amine substrates of transglutaminase, such as glutamines, lysines, or glutamines and lysines, whereby the microsphere or nanosphere can be attached to a body tissue.

According to still another aspect of the invention, a composition of matter is provided comprising a conjugate of a linking molecule that is a substrate of transglutaminase and an agent that is selected from the group consisting of a component of a ligand-receptor pair, a component of a high-affinity noncovalent binding pair and a microparticle. In this embodiment the linking molecule can be a carboxyamine substrate of transglutaminase or a hydrophobic terminal amine substrate of transglutaminase, such as lysine or known hydrophobic amine substrates.

These and other aspects of the invention are described in further detail below.

DETAILED DESCRIPTION

Figure 1:
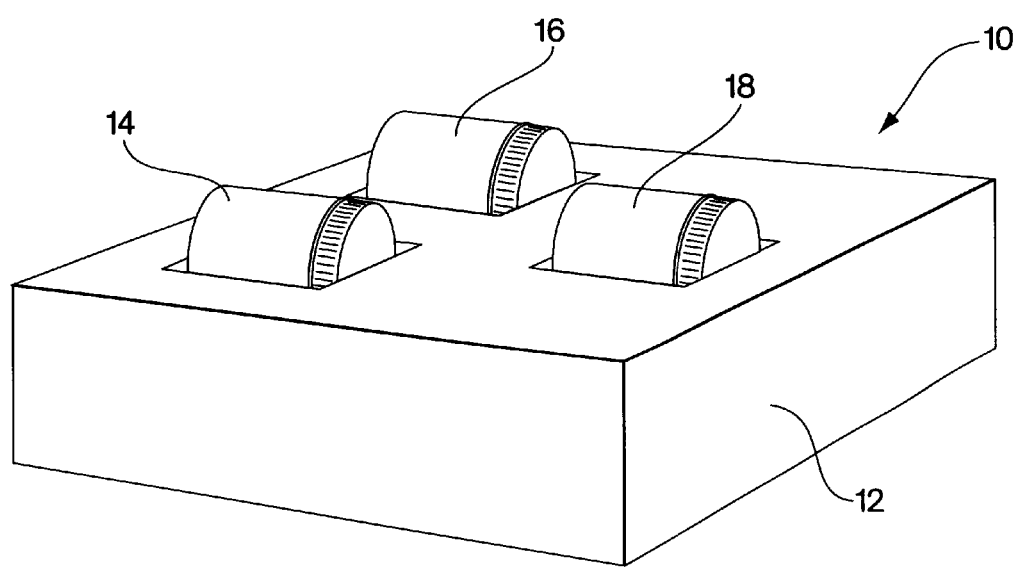
FIG. 1 depicts a kit according to the invention.

The invention is based in part on the discovery that polymers bearing multiple reactive (with transglutaminase) carboxamides or multiple reactive aliphatic amines are particularly useful linking molecules for attaching agents to protinaceous material such as skin and hair. The closest prior art teaches away from using carboxamides and also from using polymers bearing multiple reactive aliphatic amines as defined herein, for such a purpose as described in greater detail below.

In general, the agents are chemical agents and include pharmaceutical agents, enzymes, cosmetics, sunscreen agents, ligands of ligand-receptor pairs, receptors of ligand-receptor pairs, components of high affinity noncovalent bonding pairs, insecticides and repellants, bactericides, fungicides, tissue sealants, labels, structural proteins, chelating agents, microparticles and the like. Examples are listed below.

In certain embodiments the agent is a noncorneocyte, nonlabeling active agent. Thus, specifically excluded in these embodiments is corneocyte proteins. Corneocyte proteins have been shown in the prior art to be among the natural substrates of transglutaminase. In certain embodiments the agent also is a non-extracellular matrix protein agent. A non-extracellular matrix protein agent is one that is not an extracellular matrix protein. Fibronectin, an extracellular matrix protein, also has been shown in the prior art to be a substrate of transglutaminase. A nonlabeling active agent is one that is not simply a passive label with no function, when applied to a body tissue, other than being a label. Specifically excluded are labeled corneocyte proteins, labeled fibronectin, labeled extracellular matrix proteins, putrescine, dansylcadaverine, 5-(biotinamido)-pentylamine, fluoresceincadaverine and the like. Such compounds have been used in the prior art to detect on cells or cell extracts, substrates of transglutaminase.

By active agent it is meant that the agent, once coupled to a biological tissue in vivo or in vitro, has, maintains or can be released to have a desired activity such as a desired physiological activity or therapeutic activity. Examples of active agents are pharmaceutical agents, sunscreen agents, insecticides, bactericides, fungicides, etc. As used herein, an active agent is not a cosmetic agent and is not a labeling agent including diagnostic agents.

The agents are linked to proteinaceous material. When used in vivo, the agents are attached to a body tissue. Particularly important body tissues as sites of attachment are the integument (including specifically skin, nails, hair, mucous membranes and the surface of the eye), internal organs, internal tissue and wound beds. In in vitro applications, the tissue may be a body tissue, a tissue or cell isolate, isolated proteins, synthetic proteins, cell cultures and the like for use, for example, in assay systems according to the invention.

In certain embodiments, conjugates of agents and linking molecules are applied, for example, to body tissue and covalently linked to that tissue using transglutaminase.

As used herein, a conjugate means two entities stably bound to one another by any physiochemical means. It is important that the nature of the attachment be of such a nature that it does not impair substantially the effectiveness of the agent or the substrate binding ability of the linking molecule. Keeping these parameters in mind, any linkage known to those of ordinary skill in the art may be employed, covalent or noncovalent. Covalent is preferred. Such means and methods of attachment are well known to those of ordinary skill in the art.

Typically the agents used according to the invention are not themselves, in their native form, substrates for transglutaminase. Such agents, however, can be modified according to the invention to render the agent a substrate of transglutaminase. This may be accomplished for example by adding a carboxamide side group(s) to an appropriate moiety of the agent (i.e. a modified agent) or by covalently coupling glutamine, lysine or both glutamine and lysine to the agent to form a conjugate that is a substrate of transglutaminase. The most preferred method is to couple polyglutamine, polylysine, a mixed polymer of glutamine and lysine, involucrin (a natural substrate of transglutaminase) or a fragment of involucrin to the agent to form an appropriate conjugate.

Preferred linking molecules are polymers bearing multiple reactive carboxamides and/or aliphatic amines that are substrates of transglutaminase. Carboxamides that are substrates of transglutaminase are well known and include glutamines. Aliphatic amines that are substrates of transglutaminase also are well known and are exemplified in, for example, U.S. Pat. No. 5,490,980, the disclosure of which is incorporated herein by reference. Unlike the '980 patent, however, which depicts single aliphatic amine moieties and plural such moieties as independent substituents in certain circumstances, the present invention involves in one aspect using a plurality of aliphatic amines spaced apart at discrete intervals, preferably along the length of a branched or unbranched polymer. It has been discovered, surprisingly, that the spacing of the reactive moieties can be important to achieving the results of the present invention.

One embodiment involves linking molecules that are polymers having multiple units, which units each bear an aliphatic amine substrate of transglutaminase. The polymer can be a homopolymer or a heteropolymer. As used herein in connection with linking molecules, a polyaliphatic amine substrate of transglutaminase is a linking molecule with at least three aliphatic amines spaced apart from one another at discrete intervals along the backbone of the linking molecule, separated by one or more backbone atoms. This is most easily envisioned, for example, with polymers rich in lysine, whereby discrete units of the polymer carry the aliphatic amine, each being separately a substrate for transglutaminase. The linking molecule itself may be a polymer of contiguous lysines, preferably at least 3, at least 4 and at least 5 such contiguous lysines. Polymers of contiguous units, each carrying an aliphatic amine, are preferred.

The most preferred linking molecules are polymers rich in a carboxamide moiety or an aliphatic amine moiety, such as glutamine, lysine or both glutamine and lysine. A polymer rich in glutamine or lysine is a molecule wherein at least 20% of the units of the polymer carry a carboxamide, an aliphatic amine, or both, such as glutamine, lysine or glutamine and lysine, or wherein the molecule includes at least 3, preferably 4 and most preferably 5 separate and discretely spaced by a regular distance carboxamides or aliphatic amines, such as occurs with contiguous, linked glutamines or lysines. It should be understood, however, that a chain of as few as two glutamines or lysines can be attached to or tethered to an agent to render the agent a substrate of transglutaminase.

As noted above, the invention in one aspect involves attaching active agents to proteinaceous materials using transglutaminase, wherein the native agent itself is a substrate of transglutaninase. Such agents typically will be polypeptides or proteins and most typically will contain reactive glutamines, lysines or both. To determine whether an agent itself is a substrate of transglutaminase (or a modified agent, or a covalent conjugate), a simple screening method is employed.

The screening method involves selecting a nonextracellular matrix protein, nonlabeling agent, preferably an active agent, that is a substrate for transglutaminase. The agent is applied, in an isolated form, to a proteinaceous material such as a body tissue, a body tissue isolate, or more preferably, a polymer rich in glutamine, a polymer rich in lysine or a polymer rich in glutamine and lysine. Then, transglutaminase is applied to the proteinaceous material in an amount sufficient and under appropriate conditions to cross-link the agent to the proteinaceous material if the agent is a substrate of transglutaminase. Then it is determined whether the agent covalently binds to the proteinaceous material. The amounts of materials and conditions employed for these assays are derivable from the examples below and, in general, can be derived by those of ordinary skill in the art without undue experimentation from, for example, the publication by Kahlem, et al., *Proc. Natl. Acad. Sci., USA*, Vol. 93, pp. 14580–14585, December, 1996.

In constructing conjugates, it may be desirable to vary not only the number of glutamines and/or lysines in the linking molecule, but it also may be desirable to tether the linking molecule to the active agent via a spacer. This can remove, for example, any problems that might arise from steric hindrance, wherein access by transglutaminase to the reactive moiety of the linking molecule is hindered. These spacers can be any of a variety of molecules, preferably nonactive, such as straight or even branched carbon chains of $C_1$–$C_{30}$, saturated or unsaturated, phospholipids, amino acids, and in particular glycine, and the like, naturally occurring or synthetic. Additional spacers include alkyl and alkenyl carbonates, carbamates, and carbamides. These are all related and may add polar functionality to the spacers such as the $C_1$–$C_{30}$ previously mentioned.

The conjugations or modifications described herein employ routine chemistry, which chemistry does not form a part of the invention and which chemistry is well known to those skilled in the art of chemistry. The use of protecting groups and known linkers such as mono and heterobifunctional linkers are well documented in the literature and will not be repeated here.

Attachment according to the invention thus need not be directed attachment. The components of the compositions of the invention may be provided with functionalized groups to facilitate their attachment and/or linker groups may be interposed between the components of these compositions to facilitate their attachment. In addition, the components of the compositions of the present invention may be synthesized in a single process, whereby the components could be regarded as one and the same entity. For example, a protein agent may be synthesized recombinantly to include a polyglutamine at one end for linking the polypeptide via transglutaminase.

Specific examples of covalent bonds include those wherein bifunctional cross-linker molecules are used. The cross-linker molecules may be homobifunctional or heterobifunctional, depending upon the nature of the molecules to be conjugated. Homobifinctional cross-linkers have two identical reactive groups. Heterobifunctional cross-linkers are defined as having two different reactive groups that allow for sequential conjugation reaction. Various types of commercially available cross-linkers are reactive with one or more of the following groups: primary amines, secondary amines, sulphydryls, carboxyls, carbonyls and carbohydrates. Examples of amine-specific cross-linkers are bis(sulfosuccinimidyl) suberate, bis[2-(succinimidooxycarbonyloxy)ethyl] sulfone, disuccinimidyl suberate, disuccinimidyl tartarate, dimethyl adipimate.2 HCl, dimethyl pimelimidate.2 HCl, dimethyl suberimidate.2 HCl, and ethylene glycolbis-[succinimidyl-[succinate]]. Cross-linkers reactive with sulfhydryl groups include bismaleimidohexane, 1,4-di-[3'-(2'-pyridyldithio)-propionamido)]butane, 1-[p-azidosalicylamido]-4-[iodoacetamido]butane, and N-[4-(p-azidosalicylamido) butyl]-3'-[2'-pyridyldithio]propionamide. Cross-linkers preferentially reactive with carbohydrates include azidobenzoyl hydrazine. Cross-linkers preferentially reactive with carboxyl groups include 4-[p-azidosalicylamido] butylamine. Heterobifunctional cross-linkers that react with amines and sulfhydryls include N-succinimidyl-3-[2-pyridyldithio]propionate, succinimidyl[4-iodoacetyl] aminobenzoate, succinimidyl 4-[N-maleimidomethyl] cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional cross-linkers that react with carboxyl and amine groups include 1-ethyl-3-[[3-dimethylaminopropyl]-carbodiimide hydrochloride. Heterobifunctional cross-linkers that react with carbohydrates and sulfhydryls include 4-[N-maleimidomethyl]-cyclohexane-1-carboxylhydrazide.2 HCl, 4-(4-N-maleimidophenyl)-butyric acid hydrazide.2 HCl, and 3-[2-pyridyldithio] propionyl hydrazide. The cross-inkers are bis-[$-4-azidosalicylamido)ethyl]disulfide and glutaraldehyde. Amine or thiol groups may be added at any nucleotide of a synthetic nucleic acid so as to provide a point of attachment for a bifunctional cross-linker molecule. The nucleic acid may be synthesized incorporating conjugation-competent reagents such as Uni-Link AminoModifier, 3'-DMT-C6-Amine-ON CPG, AminoModifier II, N-TFA-C6-AminoModifier, C6-ThiolModifier, C6-Disulfide Phosphoramidite and C6-Disulfide CPG (Clontech, Palo Alto, Calif.).

In constructing conjugates, it also may be desirable to attach the agent to the linking molecule by a bond that cleaves under normal physiological conditions or that can be caused to cleave specifically upon application of a stimulus such as light, whereby the agent can be released. In certain instances, the agent may be inactive in its conjugated form and activated only when released. In other instances, the agent would be released to exert an activity remote from its point of attachment to the body tissue. In still other instances, the agent would be released in a sustained fashion, to prolong the release of the agent versus an agent applied to tissue but not covalently coupled to the tissue. Readily cleavable bonds include readily hydrolyzable bonds, for example, ester bonds, amide bonds and Schiff's base-type bonds. Bonds which are cleavable by light are well known.

Noncovalent methods of conjugation may also be used. Noncovalent conjugation includes hydrophobic interactions, ionic interactions, high affinity interactions such as biotin-avidin and biotin-streptavidin complexation and other affinity interactions. In one embodiment, a molecule such as avidin is attached to a linking molecule such as polyglutamine. This conjugate, once attached to tissue according to the invention, then becomes a universal linking moiety for any agent attached to a biotin molecule.

As mentioned above, the linking molecules may be part of a microparticle such as a microsphere or a nanosphere and the agent may be contained in the microparticle, either physically entrapped therein, covalently bonded thereto or otherwise physiochemically attached to the microparticle. In preferred embodiments, the microspheres or nanospheres carry, at least on their surface, polymers rich in glutamine, lysine, or both glutamine and lysine. The methods for manufacturing microparticles according to the prior art are well documented and do not form a basis for the present invention. The present invention differs from those of the prior art only in that either the polymers of the microsparticle structure themselves contain or are derivatized to contain glutamines and/or lysines, or polymers of glutamine, lysine or glutamine and lysine are included within the mixture of polymers forming the matrix, whereby such polymers are entrapped throughout and at the surface of the microparticles. Examples of microspheres and nanospheres and their method of manufacture may be found in U.S. Pat. No. 5,075,019, PCT WO95/24929, PCT WO94/23738 and PCT/US96/11990, the disclosures of which are incorporated herein by reference.

Agents in an isolated form are sometimes applied according to the invention. Isolated as used herein will depend upon the agent employed. In general, isolated as used herein means that the material is essentially free of other substances to an extent practical and appropriate for the intended use of the material. In the case of pharmaceuticals and cosmetics, the materials are likely to be substantially pure. In the case of proteins, the proteins are sufficiently pure and sufficiently free from other biological constituents of the host cells from which the proteins are derived so as to be useful in the methods according to the invention. Typically, such agents will be at least 95% or more pure.

Agents are sometimes described as native agents herein. A native agent is one as it occurs in nature (isolated or synthesized to duplicate a naturally occurring molecule), without modification or conjugation as described herein.

As mentioned above, the body tissue, to which the agents and conjugates of the invention are to be applied, may be pretreated to facilitate the reaction with transglutaminase. Such treatments include washings, abrasive treatments including physical agents such as pumice, silica and oatmeal, enzymes such as papain, bromelins and the like and chemical agents such as alpha hydroxy acids and glycolic acids. The main object is to treat the body tissue so as to expose or create reactive glutamines and/or lysines. Likewise, as mentioned above, the body tissue may be pretreated by putting down a layer or reactive groups, such as by applying to the body tissue polymers rich in lysine, glutamine or both lysine and glutamine. These materials may be attached to the body tissue by any conventional means, but, according to the invention, also may be attached using transglutaminase.

It should be noted that glutamine, lysine, and polymers of glutamine and lysine are described above. As used herein, such terms embrace nonpeptidic multimers of glutamine and lysine whereby amino acid analogs are used to replace these amino acids in the polyglutamine or polylysine substrates. Some well known classes of peptide mimetics and pseudopeptides are: azabicycloalkane amino acids; thiazabicycloalkane amino acids; oxazabicycloalkane amino acids; diazabicycloalkane amino acids. D-amino acids are an important embodiment.

The transglutaminase may be exogenously added transglutaminase or may be endogenous transglutaminase present at the tissue.

In one embodiment transglutaminase is used to glue two tissues to one another. This can be accomplished in a variety of ways. Transglutaminase, a substrate of transglutaminase, or both can be supplied to the surfaces of two tissues which then are held in contact with one another for a period of time sufficient to permit transglutaminase to crosslink the tissues to one another. In one circumstance, exogenously supplied transglutaminase is applied to the surfaces of the tissues to crosslink substrates of transglutaminase to one another, which substrates are present and are endogenous on the surfaces of the tissue. In another circumstance, exogenously supplied substrates of transglutaminase are applied to the surfaces of the tissues and are acted upon by endogenous transglutaminase to crosslink the tissue surfaces to one another. In another circumstance both transglutaminase and substrate of transglutaminase are applied to the surfaces of the tissue to crosslink the surfaces to one another. In this situation, a single substrate such as polyglutamine could be applied, one end attaching to one surface and the other end attaching to the opposing surface of the tissues to be crosslinked to one another. Alternatively, a first substrate (a linking molecule such as polyglutamine) could be applied to create first reactive surfaces and a second substrate (a complementary linking molecule such as polylysine) could be applied to crosslink the primary linking molecules on opposing surfaces to one another.

The invention also involves kits. Referring to FIG. 1, the kit is a package 10 comprising a housing 12 holding a first container 14, a second container 16 and a third container 18. The first container can contain any of the agents or conjugates that are substrates of transglutaminase, as described above. The second container can contain transglutaminase. The third container can contain, for example, a linking molecule for preparing the surface of the body tissue for application of the agents and conjugates of the invention. The transglutaminase preferably is stored in the presence of a chelating agent such as EDTA, and either one of the first or third containers contains calcium for activating the transglutaminase when applied to the tissue. The various containers may also contain preservatives, buffers, vehicles, and the like, as is conventional. The package also may house instructions for using the materials according to the invention.

The conjugates and agents of the invention are applied in effective amounts. An effective amount, in general, means that amount necessary to achieve the purpose for which the agent is applied. If the agent is a pharmaceutical agent, then the amount is that amount necessary to delay the onset of, slow the progression of, halt altogether the onset or progression of or diagnose a particular condition being treated. In the case of a cosmetic agent, the effective amount will be that amount necessary to achieve the desired cosmetic result. In the case of a sunscreen agent, an effective amount will be that amount necessary to achieve suitable protection from the sun as is conventional. Effective amounts will, of course, depend on the particular condition being treated, severity of the condition, the needs of the patient, individual patient parameters including age, physical condition, size and weight, concurrent treatment, frequency of treatment and mode of treatment. These factors are well-known to those of ordinary skill in the art and can be addressed with no more than routine experimentation. The mode of delivery typically will be topical. Other modes of delivery are, nonetheless, appropriate depending on the condition being treated. Aerosols are an example of an appropriate mode of delivery.

The agent may be a sunscreen agent. Examples of sunscreen agents include: p-aminobenzoate analogs such as 2-ethylhexyl-4-dimethylaminobenzoate (Padimate O); p-methoxy-2-ethyl-hexyl-cinnamate (Parsol 1789); oxybenzone (benzophenone-3); ethylhexylsalicylate; diphenylacrylate polyisobutylene; alkyl-$,$-diphenylacrylate and "-cyano-$,$-diphenylacrylate; 1-(4-aminophenyl)-2-morpholinylethanone; (1-(4-methoxylphenyl)-3-(4-tert-butyl-phenyl)propan-1-3-dione; methyl anthranilate; octocrylene; Tretinoin "-hydroxyacid; diphenylacrylate polyisobutylene; 1-(4-aminophenyl)-2-morpholinylethanone; diphenylacrylate polyisobutylene; digalloyl trioleate; glyceryl p-aminobenzoate; 4-(omega -dialkylaminoalkoxy)phenylmethylene)-1,3,3-trimethyl-2-oxabicyclo(2.2.2)octan-6-ones; 5-(arylmethylene)-1,3,3-trimethyl-2-oxabicyclo(2.2.2)octan-6-ones; melanin.

The agent may also be a cosmetic agent. Examples of cosmetic components include: Vitamin C; Alpha -tocopherol (Vit. E analog); Ammonium lauryl Sulfate; Cocamidopropyl Betaine; Lauramide DEA; Cocamide DEA; Methyl paraben; Propyl paraben; Butyl paraben; Salicylic acid; Propylene glycol; EDTA; BHT; BHA; TBHQ; DMDM hydantoin; Imidazolidinyl urea; Potassium sorbate; Sodium Benzoate; phenoxyethanol; Polysorbate 20 and 80; Sodium laurylether sulfate; Oleyl betaine; Tego betaine; Sorbitol; Glycerin monolaurate; Glycerol stearate.

A preferred cosmetic agent is any of the known bulking agents which can be added to the hair or nails to provide 'body' and strength. Cationic surfactant/polymers, fatty alcohols (non-ionic surfactant), waxes or esters, non-ionic polymers (e.g. polyglycols) for thickening, and insoluble silicone. The preferred bulking agent is the cationic surfactant, which places a dispersive charge on the hair. Additional bulking agents can be solutions of proteins, peptides, and polynucleotides or combinations thereof. Particular bulking agents include collagen, keratins, plant structural proteins, silk, fibrin, mucopolysaccharide and elastin. Bulking agents are well known to those of ordinary skill in the art.

The agent also can be a tissue sealant. Tissue sealants are those used in wound healing to mechanically seal wounds. The use of transglutaminase to covalently attach such materials would add mechanical and adhesive strength to this sealant. Such tissue sealants are composed typically of fibrinogen, collagen, hyaluronic acid, synthetic peptides and the like. They also can be polyglutamines, polylysines, or polymers of both glutamine and lysine, corneocyte proteins and the like.

The agents also can be insect repellants. A widely used insect repellant is N-N-diethyl-3-methylbenzamide. The agent also may be cultured cells and cultured body tissues used for wound healing, cartilage replacement, corneal replacements and other like surgical procedures.

As mentioned above, the agent may be a pharmaceutical agent.

When administered the pharmaceutical agents of the invention are applied in pharmaceutically acceptable amounts and in pharmaceutically acceptable compositions. Such preparations may routinely contain salts, buffering agents, preservatives, compatible carriers and optionally other therapeutic or nontherapeutic ingredients. When used in medicine, the salts should be pharmaceutically acceptable, but nonpharmaceutically acceptable salts may conveniently be used to prepare pharmaceutically acceptable salts thereof and are not excluded from the scope of the invention.

Examples of categories of pharmaceutical agents include: analgesic; amino acid; antagonist; anti-acne agent; anti-allergic; anti-asthmatic; antibacterial; anticholinergic; antifungal; antiglaucoma agent; antihistamine; anti-infective; anti-infective, topical; anti-inflammatory; antikeratinizing agent; antimicrobial; antimycotic; antineoplastic, antineutropenic; antiproliferative; antipruritic; antiseborrheic; carbonic anhydrase inhibitor; cholinergic; cholinergic agonist; diagnostic aids; ectoparasiticide; fluorescent agent; glucocorticoid; hair growth stimulant; histamine H2 receptor antagonists; immunizing agent; immunomodulator; immunoregulator; immunostimulant; immunosuppressant; keratolytic; mucosal protective agent; radio; wound healing agent.

Analgesic: Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lornoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propiram Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium Zucapsaicin.

Antiacne: Adapalene; Erytiromycin Salnacedin; Inocoterone Acetate.

Antiallergic: Amlexanox; Astemizole; Azelastine Hydrochloride; Eclazolast; Minocromil; Nedocromil; Nedocromil Calcium; Nedocromil Sodium; Nivimedone Sodium; Pemirolast Potassium; Pentigetide; Pirquinozol; Poisonoak Extract; Probicromil Calcium; Proxicromil; Repirinast; Tetrazolast Meglumine; Thiazinamium Chloride; Tiacrilast; Tiacrilast Sodium; Tiprinast Meglumine; Tixanox.

Antiasthmatic: Ablukast; Ablukast Sodium; Azelastine Hydrochloride; Bunaprolast; Cinalukast; Cromitrile Sodium; Cromolyn Sodium; Enofelast; Isamoxole; Ketotifen Fumarate; Levcromakalim; Lodoxamide Ethyl; Lodoxamide Tromethamine; Montelukast Sodium; Ontazolast; Oxarbazole; Oxatomide; Piriprost; Piriprost Potassium; Pirolate; Pobilukast Edamine; Quazolast; Repirinast; Ritolukast; Sulukast; Tetrazolast Meglumine; Tiaramide Hydrochloride; Tibenelast Sodium; Tomelukast; Tranilast; Verlukast; Verofylline; Zarirlukast.

Antibacterial: Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin, Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodiumn; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefinetazole; Cefinetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifiurthiazole; Nitrocycline; Nitrofurantoin; Nitromide; Norfloxacin; Novobiocin Sodium; Ofloxacin; Onnetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin.

Anticholinergic: Alverinc Citrate; Anisotropine Methylbromide; Atropine; Atropine Oxide Hydrochloride; Atropine Sulfate; Belladonna; Benapryzine Hydrochloride; Benzetimide Hydrochloride; Benzilonium Bromide; Biperiden; Biperiden Hydrochloride; Biperiden Lactate; Clidinium Bromide; Cyclopentolate Hydrochloride; Dexetimide; Dicyclomine Hydrochloride; Dihexyverine Hydrochloride; Domazoline Fumarate; Elantrine; Elucaine; Ethybenztropine; Eucatropine Hydrochloride; Glycopyrrolate; Heteronium Bromide; Homatropine Hydrobromide; Homatropine Methylbromide; Hyoscyamine; Hyoscyamine Hydrobromide; Hyoscyamine Sulfate; Isopropamide Iodide; Mepenzolate Bromide; Methylatropine Nitrate; Metoquizine; Oxybutynin Chloride; Parapenzolate Bromide; Pentapiperium Methylsulfate; Phencarbamide; Poldine Methylsulfate; Proglumide; Propantheline Bromide; Propenzolate Hydrochloride; Scopolamine Hydrobromide; Tematropium Methylsulfate; Tiquinamide Hydrochloride; Tofenacin Hydrochloride; Toquizine; Triampyzine Sulfate; Trihexyphenidyl Hydrochloride; Tropicamide.

Antifungal: Acrisorcin; Ambruticin; Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofimgin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofungin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifimgin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafungin; Undecylenic Acid; Viridofulvin; Zinc Undecylenate; Zinoconazole Hydrochloride.

Antiglaucoma agent: Alprenoxime Hydrochloride; Colforsin; Dapiprazole Hydrochloride; Dipivefrin Hydrochloride; Naboctate Hydrochloride; Pilocarpine; Pirnabine.

Antihistaminic: Acrivastine; Antazoline Phosphate; Astemizole; Azatadine Maleate; Barmastine; Bromodiphenhydramine Hydrochloride; Brompheniramine Maleate; Carbinoxamine Maleate; Cetirizine Hydrochloride; Chlorpheniramine Maleate; Chlorpheniramine Polistirex; Cinnarizine; Clemastine; Clemastine Fumarate; Closiramine Aceturate; Cycliramine Maleate; Cyclizine; Cyproheptadine Hydrochloride; Dexbrompheniramine Maleate; Dexchlorpheniramine Maleate; Dimethindene Maleate; Diphenhydramine Citrate; Diphenhydramine Hydrochloride; Dorastine Hydrochloride; Doxylamine Succinate; Ebastine; Levocabastine Hydrochloride; Loratadine; Mianserin Hydrochloride; Noberastine; Orphenadrine Citrate; Pyrabrom; Pyrilamine Maleate; Pyroxamine Maleate; Rocastine Hydrochloride; Rotoxamine; Tazifylline Hydrochloride; Temelastine; Terfenadine; Tripelennamine Citrate; Tripelennamine Hydrochloride; Triprolidine Hydrochloride; Zolamine Hydrochloride .

Anti-infective: Difloxacin Hydrochloride; Lauryl Isoquinolinium Bromide; Moxalactam Disodium; Ornidazole; Pentisomicin; Sarafloxacin Hydrochloride; Protease inhibitors of HIV and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); Ciprofloxacin (Cipro).

Anti-infective, topical: Alcohol; Aminacrine Hydrochloride; Benzethonium Chloride: Bithionolate Sodium; Bromchlorenone; Carbamide Peroxide; Cetalkonium Chloride; Cetylpyridinium Chloride: Chlorhexidine Hydrochloride; Clioquinol; Domiphen Bromide; Fenticlor; Fludazonium Chloride; Fuchsin, Basic; Furazolidone; Gentian Violet; Halquinols; Hexachlorophene: Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofurazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal: Troclosene Potassium.

Anti-inflammatory: Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone ; Sermetacin; Sudoxicam; Sulindac; Suprofen; Talmetacin; Talniflumate; Talosalate; Tebufelone ; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium Antikeratinizing agent: Doretinel; Linarotene; Pelretin.

Antimicrobial: Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine.

Antimycotic: Amorolfine.

Antineoplastic: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine: Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1;Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ornaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogennanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B;

mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Anti-cancer Supplementary Potentiating Agents: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL. The compounds of the invention also can be administered with cytokines such as granulocyte colony stimulating factor.

Antineutropenic: Filgrastim; Lenograstim; Molgramostim; Regramostim; Sargramostim.

Antiproliferative agent: Piritrexim Isethionate.

Antiprotozoal: Amodiaquine; Azanidazole; Bamnidazole; Camidazole; Chlortetracycline Bisulfate; Chlortetracycline Hydrochloride; Flubendazole; Flunidazole; Halofuginone Hydrobromide; Imidocarb Hydrochloride; Ipronidazole; Metronidazole; Misonidazole; Moxnidazole; Nitarsone; Partricin; Puromycin; Puromycin Hydrochloride; Ronidazole; Sulnidazole; Tinidazole.

Antipruritic: Cyproheptadine Hydrochloride; Methdilazine; Methdilazine Hydrochloride; Trimeprazine Tartrate.

Antipsoriatic: Acitretin; Anthralin; Azaribine; Calcipotriene; Cycloheximide; Enazadrem Phosphate; Etretinate; Liarozole Fumarate; Lonapalene; Tepoxalin.

Carbonic anhydrase inhibitor: Acetazolamide; Acetazolamide Sodium; Dichlorphenamide; Dorzolamide Hydrochloride; Methazolamide; Sezolamide Hydrochloride.

Cholinergic: Aceclidine; Bethanechol Chloride; Carbachol; Demecarium Bromide; Dexpanthenol; Echothiophate Iodide; Isoflurophate; Methacholine Chloride; Neostigmine Bromide; Neostigmine Methylsulfate; Physostigmine; Physostigmine Salicylate; Physostigmine Sulfate; Pilocarpine; Pilocarpine Hydrochloride; Pilocarpine Nitrate; Pyridostigmine Bromide.

Diagnostic aid: Aminohippurate Sodium; Anazolene Sodium; Arclofenin; Arginine; Bentiromide; Benzylpenicilloyl Polylysine; Butedronate Tetrasodium; Butilfenin; Coccidioidin; Corticorelin Ovine Triflutate; Corticotropin, Repository; Corticotropin Zinc Hydroxide; Diatrizoate Meglumine; Diatrizoate Sodium; Diatrizoic Acid; Diphtheria Toxin for Schick Test; Disofenin; Edrophonium Chloride; Ethiodized Oil; Etifenin; Exametazime; Ferristenc; Ferumoxides; Ferumoxsil; Fluorescein; Fluorescein Sodium; Gadobenate Dimeglumine; Gadoteridol; Gadodiamide; Gadopentetate Dimegiumine; Gadoversetamide; Histoplasmin; Impromidine Hydrochloride; Indigotindisulfonate Sodium; Indocyanine Green; Iobenguane Sulfate I 123; Iobenzamic Acid; Iocarmate Meglumine; Iocarmic Acid; Iocetamic Acid; Iodamide; Iodamide Megiumine; Iodipamide Meglumine; Iodixanol; Iodoxamate Meglumine; Iodoxamic Acid; Ioglicic Acid; Ioglucol; Ioglucomide; Ioglycamic Acid; Iogulamide; Iohexol; Iomeprol; Iopamidol; Iopanoic Acid; Iopentol; Iophendylate; Iprofenin; Iopronic Acid; Ioprocemic Acid; Iopydol; Iopydone; Iosefamic Acid; Ioseric Acid; Iosulamide Meglumine; Iosumetic Acid; Iotasul; Iotetric Acid; Iothalamate Meglumine; Iothalamate Sodium; Iothalamic Acid; Iotrolan; Iotroxic Acid; Ioversol; Ioxaglate Meglumine; Ioxagiate Sodium; Ioxaglic Acid; Ioxilan; Ioxotrizoic Acid; Ipodate Calcium; Ipodate Sodium; Isosulfan Blue; Leukocyte Typing Serum; Lidofenin; Mebrofenin; Meglumine; Metrizamide; Metrizoate Sodium; Metyrapone; Metyrapone Tartrate; Mumps Skin Test Antigen; Pentetic Acid; Propyliodone; Quinaldine Blue; Schick Test Control; Sermorelin Acetate; Sodium Iodide I 123; Sprodiamide; Stannous Pyrophosphate; Stannous Sulfur Colloid; Succimer; Teriparatide Acetate; Tetrofosmin; Tolbutamide Sodium; Tuberculin; Tyropanoate Sodium; Xylose.

Ectoparasiticide: Nifluridide; Permethrin.

Glucocorticoid: Amcinonide; Beclomethasone Dipropionate; Betamethasone; Betamethasone Acetate;

Betamethasone Benzoate; Betamethasone Dipropionate; Betamethasone Sodium Phosphate; Betamethasone Valerate; Carbenoxolone Sodium; Clocortolone Acetate; Clocortolone Pivalate; Cloprednol; Corticotropin; Corticotropin, Repository; Corticotropin Zinc Hydroxide; Cortisone Acetate; Cortivazol; Descinolone Acetonide; Dexamethasone; Dexamethasone Sodium Phosphate; Diflucortolone; Diflucortolone Pivalate; Flucloronide; Flumethasone; Flumethasone Pivalate; Flunisolide; Fluocinolone Acetonide; Fluocinonide; Fluocortolone; Fluocortolone Caproate; Fluorometholone; Fluperolone Acetate; Fluprednisolone; Fluprednisolone Valerate; Flurandrenolide; Formocortal; Hydrocortisone; Hydrocortisone Acetate; Hydrocortisone Buteprate; Hydrocortisone Butyrate; Hydrocortisone Sodium Phosphate; Hydrocortisone Sodium Succinate; Hydrocortisone Valerate; Medrysone; Methylprednisolone; Methylprednisolone Acetate; Methylprednisolone Sodium Phosphate; Methylprednisolone Sodium Succinate; Nivazol; Paramethasone Acetate; Prednicarbate; Prednisolone; Prednisolone Acetate; Prednisolone Hemisuccinate; Prednisolone Sodium Phosphate; Prednisolone Sodium Succinate; Prednisolone Tebutate; Prednisone; Prednival; Ticabesone Propionate; Tralonide; Triamcinolone; Triamcinolone Acetonide; Triamcinolone Acetonide Sodium; Triamcinolone Diacetate; Triamcinolone Hexacetonide.

Hair growth stimulant: Minoxidil.

Histamine H2 receptor antagonists: Ranitidine (Zantac); Famotidine (Pepcid); Cimetidine (Tagamet); Nizatidine (Axid).

Immunizing agent: Antirabies Serum; Antivenin (Latrodectus mactans); Antivenin (Micrurus Fulvius); Antivenin (Crotalidae) Polyvalent; BCG Vaccine; Botulism Antitoxin; Cholera Vaccine; Diphtheria Antitoxin; Diphtheria Toxoid; Diphtheria Toxoid Adsorbed; Globulin, Immune; Hepatitis B Immune Globulin; Hepatitis B Virus Vaccine Inactivated; Influenza Virus Vaccine; Measles Virus Vaccine Live; Meningococcal Polysaccharide Vaccine Group A; Meningococcal Polysaccharide Vaccine Group C; Mumps Virus Vaccine Live; Pertussis Immune Globulin; Pertussis Vaccine; Pertussis Vaccine Adsorbed; Plague Vaccine; Poliovirus Vaccine Inactivated; Poliovirus Vaccine Live Oral; Rabies Immune Globulin; Rabies Vaccine; $Rh_o(D)$ Immune Globulin; Rubella Virus Vaccine Live; Smallpox Vaccine; Tetanus Antitoxin; Tetanus Immune Globulin; Tetanus Toxoid; Tetanus Toxoid Adsorbed; Typhoid Vaccine; Yellow Fever vaccine; Vaccinia Immune Globulin; Varicella-Zoster Immune Globulin.

Immunomodulator: Dimepranol Acedoben; Imiquimod; Interferon Beta-1b; Lisofylline; Mycophenolate Mofetil; Prczatide Copper Acetate.

Immunoregulator: Azarole; Fanetizole Mesylate; Frentizole; Oxamisole Hydrochloride; Ristianol Phosphate; Thymopentin; Tilomisole.

Immunostimulant: Loxoribine; Teceleukin.

Immunosuppressant: Azathioprine; Azathioprine Sodium; Cyclosporine; Daltroban; Gusperimus Trihydrochloride; Sirolimus; Tacrolimus. Mucolytic: Acetylcysteine; Carbocysteine; Domiodol.

Mucosal Protective agents: Misoprostol (Cytotec).

Radioactive agent: Fibrinogen 1 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine 1 131; Liothyronine I 125; Liothyronine I 131; Merisoprol Acetate Hg 197; Merisoprol Acetate Hg 203; Merisoprol Hg 197; Selenomethionine Se 75; Technetium Tc 99 m Antimony Trisulfide Colloid; Technetium Tc 99 m Bicisate; Technetium Tc 99 m Disofenin; Technetium Tc 99 m Etidronate; Technetium Tc 99 m Exametazime; Technetium Tc 99 m Furifosmin; Technetium Tc 99 m Gluceptate; Technetium Tc 99 m Lidofenin; Technetium Tc 99 m Mebrofenin; Technetium Tc 99 m Medronate; Technetium Tc 99 m Medronate Disodium; Technetium Tc 99 m Mertiatide; Technetium Tc 99 m Oxidronate; Technetium Tc 99 m Pentetate; Technetium Tc 99 m Pentetate Calcium Trisodium; Technetium Tc 99 m Sestamibi; Technetium Tc 99 m Siboroxime; Technetium Tc 99 m Succimer; Technetium Tc 99 m Sulfur Colloid; Technetium Tc 99 m Teboroxime; Technetium Tc 99 m Tetrofosmin; Technetium Tc 99 m Tiatide; Thyroxine 1 125; Thyroxine 1 131; Tolpovidone 1 131; Triolein 1 125; Triolein 1 131.

Wound healing agent: Ersofermin.

The invention thus may be used, inter alia, to localize drugs to a tissue such as a wound bed or for localized delivery to a tissue, to hold a drug, insect repellant, bactericide fungicide, growth factors, cytokine, and the like at a particular location to prevent the drug from being flushed away to other body sites where it is not needed, to apply bulking agents and other cosmetic agents to the integuments, such as the skin, hair and nails, to hold sunscreen agents at the surface of the skin for longer periods of time, to hold anti-nerve gas enzymes at the surface of the skin whereby nerve gas can be deactivated, to hold or link chemical agents to the skin which can in turn act as binding sites for other agent or alternatively, as reactive sites for catalytic buildup of multiple alternating layers, to link hydrophobic compounds to the skin, thereby making the skin hydrophobic, to link conditioners to the hair, thereby giving hair the appearance of greater bulk and to link agents to organs or tissues which are to be transplanted.

EXAMPLES

Example 1

Durable Suntan Preparation and Kit.

A kit is provided for producing a durable sunscreen. The kit includes as a first component a conjugate of a low molecular weight sunscreen agent and a linking agent. This component is an aqueous solution, pH 6.4 of 50 mM polylysyl-methoxy-2-ethylhexyl-cinnamate, 0.1 v % propylene glycol, 0.5 mM, EDTA, 0.1 wt % BHT, 0.1 wt % potassium sorbate, 0.05 wt % polysorbate 20 and 80 and 1 mM sodium laurylether sulfate. Component 2 of the kit is a calcium chloride activator solution. This is an aqueous solution at about 25 mM calcium chloride. Component 3 of the kit is lyophilized transglutaminase. The lyophilized preparation can contain 10 mg of recombinant tissue transglutaminase in 2% sucrose, 0.1 mM EDTA, and 5 mM glycine buffer, pH 7.2.

Three vials containing the three kit components are opened. About 10 mL of component 1 is added to 10 mg of component 3, and the combination is mixed by swirling. Then this combination is added to about 90 mL of component 1. Finally, about 10 mL of component 2 is added to the mixture, with this final combination mixed by gentle swirling. The mixture then is applied to a washed and scraped skin surface. The mixture is uniformly spread on the skin and allowed to remain for ten minutes. The excess solution is removed by washing.

Example 2
Durable Topical Antifungal Preparation and Kit.

A kit is provided for producing durable antifungal protection. The kit contains three components. Component 1 is a conjugate of an antifungal agent and a linking agent. This component is an aqueous solution, pH 6.4, containing 0.01 wt % polylysyl-amphotericin B conjugate, 10 v % ethanol, 0.1 v % propylene glycol, 0.5 mM EDTA, 0.1 wt % BHT. Component 2 is a calcium chloride activator solution as described for Example 1. Component 3 is a lyophilized transglutaminase preparation as described in Example 1. The three containers containing components 1, 2 and 3 are opened. Ten mL of component 1 is added to component 3, and they are mixed by swirling. The mixture then is added to about 90 mL of component 1. To this mixture is added component 2. This final combination is mixed by gentle swirling. After this, the material is applied to the surface of skin as described in Example 1.

Example 3
Long-Term Protective Preparation for Anticholinesterase Nerve Gas and Kit.

A kit for providing long-term protection from anticholinesterase nerve gas is provided. Component 1 of the kit includes recombinant cholinesterase coupled to biotin (e.g., by reaction in the presence of N.N. succinimide). Component 2 is polyglutamine coupled to avidin. Component 2 is applied to the surface of the skin in the presence of transglutaminase, as described above in connection with Examples 1 and 2. After the avidin is coupled to the skin via the polyglutamine, then component 1 is added to bind the biotin to the avidin, thereby coupling the cholinesterase to the skin.

Example 4
A Mousse for Thickening Hair.

A dispensing can with three reservoirs (a calcium ion solution, a transglutaminase solution and a hair bulking or thickening agent such as a mucopolysaccharide linked to polyglutamine) is provided. The three solutions are mixed, as is conventional with such dispensing cans, as they are being applied onto tissue such as hair. The mousse can be combed through the hair, left on the hair for at least ten minutes, and then rinsed.

Example 5

It has been shown in previous studies that polyglutamine attached to other peptides remains an excellent substrate of transglutaminase. Under optimal conditions, virtually all of the glutamine residues acted as amine acceptors in the reaction with an aliphatic amine, and lengthening the sequence of polyglutamine increases the reactivity of each glutamine residue. In the presence of transglutaminase, peptides containing polyglutamine become cross-linked to polylysine. The details of the reaction conditions and the manner of applying labels whereby the reaction may be visualized under UV light are described in detail in Kahlem et al., *Proc. Natl. Acad. Sci. USA,* 1996 93:14580–14585 (Appendix A). The same polyglutamines, but attached to agents as described herein, and, in general, the same conditions as described in Kahlem et al. may be applied in the above-described examples and, in general, in the-practice of the present invention. The disclosure of this reference, as well as any other reference mentioned herein, is incorporated by reference in its entirety.

Figure 2:
FIG. 2 depicts the skin of a mouse treated according to the invention.

Example 6
Polyglutamine Containing a Fluorescent Marker is Covalently Attached to the Surface of the Skin Through the Action of Transglutaminase A. Mouse was epilated. Seven days later, a concentrated reaction solution containing guinea pig transglutaminase, dansyl labeled polyglutamine and $Ca^{2+}$ at 10 mM was applied to the left side (FIG. 2). The control (right side) was pretreated for 10 mins with 100 mM cystamine, the excess liquid was drained and the same reaction solution containing 25 mM cystamine was applied. After 30 minutes, both sites were washed with a solution of 1% SDS. The mouse was then photographed under UV illumination (312 nm). The left side shows strong fluorescence of dansyl polyglutamine whereas the right side shows very weak fluorescence (FIG. 2).

Figure 3:
FIG. 3 depicts the mouse of FIG. 2 after 10 days.

B. Same mouse was photographed again five days later. There is still considerable fluorescence at the site of enzymatic coupling (left, FIG. 3), but the control fluorescence (right, FIG. 3) has virtually disappeared.

Reaction Solution

10 µl buffer containing 100 uM Tris pH8.2, 10 MN $CaCl_2$, and 10 mM DTT

3 µl dansylated polyglutamine (5 uM)

3 µl (13.3 mU/µl) partially purified guinea pig transglutaminase

We claim:

1. A method for attaching a non-corneocyte protein, nonlabeling agent to a body tissue comprising:
    applying to the body tissue a conjugate of the agent and a carboxamide-containing linking molecule having at least two contiguous linked glutamines and being a substrate of transglutaminase,
    said applying to the body tissue being carried out in the presence of transglutaminase in an amount effective to covalently crosslink the conjugate to the body tissue via the linking molecule, and
    allowing said crosslinking to occur.

2. The method of claim 1, wherein the linking molecule is selected from the group consisting molecules having:
    (a) at least three contiguous linked glutamines,
    (b) at least four contiguous linked glutamines, and
    (c) at least five contiguous linked glutamines.

3. The method of claim 1, wherein the linking molecule comprises 5 or more contiguous glutamines attached directly to one another by peptide bonds.

4. The method of claim 1, wherein the linking molecule comprises a polymer of amino acids and wherein at least 20% of the amino acids are glutamines.

5. The method of claim 4, wherein at least 30% of the amino acids are glutamines.

6. The method of claim 4, wherein at least 40% of the amino acids are glutamines.

7. The method of claim 1, further comprising first attaching to the body tissue a complementary linking molecule bearing multiple reactive aliphatic amines, the complementary linking molecule being an aliphatic amine substrate of transglutaminase, wherein the conjugate is crosslinked to the body tissue by crosslinking the aliphatic amines of the complementary linking molecule and the carboxamide of linking molecule to one another by said transglutaminase.

8. The method of claim 7, wherein the complementary linking molecule is attached to the body tissue by
    applying to the body tissue the complementary linking molecule,
    applying to the body tissue an amount of transglutaminase effective for crosslinking the complementary linking molecule to the body tissue, and
    allowing said crosslinking to occur.

9. The method of claim 8, wherein a polymer rich in lysine is the complementary linking molecule.

10. The method of claim 9, wherein the linking molecule is a polymer having 4 or more contiguous glutamines directly attached to one another by peptide bonds.

11. The method of claim 9, wherein the polymer rich in lysine has 4 or more contiguous lysines directly attached to one another by peptide bonds.

12. The method of claim 1, wherein the agent is not itself a substrate of transglutaminase.

13. The method of claim 1, wherein the body tissue is selected from the group consisting of skin, hair, nails, wound bed tissue and internal body tissue.

14. The method of claim 1, wherein the body tissue is selected from the group consisting of skin, hair and nails, and wherein the agent is selected from the group consisting of a cosmetic agent, a bulking agent, a sunscreen agent, a coloring agent, a pharmaceutical agent, a ligand-receptor complex and a receptor of a ligand-receptor complex.

15. The method of claim 1, wherein the agent is an enzyme.

16. The method of claim 15, wherein the agent is selected from the group consisting of a cholinesterase and a phosphodiesterase.

17. The method of claim 14, wherein crosslinking forms a bond between the agent and the linking molecule that is hydrolyzable under normal physiological conditions.

18. The method of claim 1, wherein the agent is a nonprotein.

19. The method of claim 18, wherein the agent is not itself a substrate for transglutaminase.

20. A method for attaching an agent to a body tissue comprising first attaching to the body-tissue a carboxamide-containing linking molecule having at least two contiguous linked glutamines that is covalently bondable to the agent in the presence of transglutaminase, then applying to the body tissue having the linking molecule attached thereto an agent that is a substrate of transglutaminase and that is covalently bondable to the linking molecule in the presence of transglutaminase, applying to the body tissue transglutaminase in an amount effective in crosslinking the agent to the linking molecule, and allowing said crosslinking to occur.

21. The method of claim 20, wherein the linking molecule is a substrate of transglutaminase and wherein the linking molecule is attached to the body tissue by applying to the body tissue the linking molecule, applying to the body tissue transglutaminase in an amount effective to crosslinking the linking molecule to the body tissue, and allowing said crosslinking to occur.

22. The method of claim 20, wherein the linking molecule is a polymer having multiple units that is a substrate of transglutaminase.

23. The method of claim 22, wherein the agent comprises a polymer having multiple units which carry an aliphatic amine that is a substrate of transglutaminase.

24. The method of claim 23, wherein the agent comprises a polymer rich in lysine.

25. The method of claim 20, wherein the agent is selected from the group consisting of a visible label of a high affinity noncovalent coupling pair, a pharmaceutical agent, a receptor or a ligand of a receptor/ligand pair, a cosmetic, and a sunscreen agent.

26. The method of any one of claim 20, wherein the body tissue is selected from the group consisting of skin, hair, nails, wound bed tissue and internal body tissue.

27. The method of claim 20, wherein the agent in a nonprotein.

28. The method of claim 20, wherein the agent is an enzyme.

29. The method of claim 28, wherein the enzyme is selected from the group consisting of a cholinesterase and a phosphodiesterase.

30. A method for attaching an agent to a body tissue comprising first attaching to the body tissue a carboxamide-containing linking molecule having at least two contiguous linked glutamines that is covalently bondable to the agent in the presence of transglutaminase, then applying to the body tissue having the linking molecule attached thereto an agent that is a substrate of transglutaminase and that is covalently bonded to the linking molecule in the presence of transglutaminase, said applying to the body tissue being carried out in the presence of a sufficient amount of transglutaminase effective to covalently crosslink the agent to the linking molecule, and allowing the crosslinking to occur.

31. The method of claim 30, wherein the linking molecule is a polymer having multiple units that is a substrate of transglutaminase.

32. The method of claim 31, wherein the agent comprises a polymer having multiple units which carry an aliphatic amine that is a substrate of transglutaminase.

33. The method of claim 31, wherein the agent comprises a polymer rich in lysine.

34. The method of claim 30, wherein the agent is selected from the group consisting of a visible label, a component of a high affinity noncovalent coupling pair, a receptor or a ligand of a receptor/ligand pair, a pharmaceutical agent, a cosmetic agent and a sunscreen agent.

35. The method of claim 30, wherein the body tissue is selected from the group consisting of, skin, hair, nails, wound bed tissue and internal body tissue.

36. The method of claim 30, wherein the agent is a nonprotein.

37. The method of claim 30, wherein the agent is an enzyme.

38. The method of claim 37, wherein the enzyme is selected from the group consisting of a cholinesterase and a phosphodiesterase.

39. A method for attaching a nonextracellular matrix protein agent to a body tissue comprising:

applying to the body tissue a conjugate of the agent and a linking molecule having at least three contiguous lysines attached directly to one another by peptide bonds, said applying to the body tissue being carried out in the presence of transglutaminase in an amount effect to covalently crosslink the linking molecule to the body tissue, and allowing the crosslinking to occur.

40. The method of claim 39, wherein the linking molecule is selected from the group consisting of molecules having at least 4 and at least 5 contiguous lysines attached directly to one another by peptide bonds.

41. The method of claim 39, wherein the linking molecule is a polymer selected from the group consisting of polymers containing at least 20% lysines, at least 30% lysines, and at least 40% lysines.

42. The method of claim 39, wherein the agent is selected from the group consisting of a component of a high affinity noncovalent coupling pair, a receptor or a ligand of a receptor/ligand pair, a pharmaceutical agent, a cosmetic agent and a sunscreen agent.

43. The method of claim 39, wherein the body tissue is selected from the group consisting of skin, hair, nails, wound bed tissue and internal body tissue.

44. The method of claim 39, wherein the agent is not itself a substrate of transglutaminase.

45. The method of claim 39, wherein the agent is a nonprotein.

46. The method of claim 39, wherein the agent is an enzyme.

47. The method of claim 46, wherein the enzyme is selected from the group consisting of a cholinesterase and a phosphodiesterase.

48. The method of claim 1 or 39, wherein the transglutaminase is exogenously added transglutaminase.

* * * * *

UNITED STATES PATENT AND TRADEMARK OFFICE
CERTIFICATE OF CORRECTION

PATENT NO. : 6,267,957 B1
DATED : July 31, 2001
INVENTOR(S) : Howard Green et al.

It is certified that error appears in the above-identified patent and that said Letters Patent is hereby corrected as shown below:

Column 27,
Line 52, delete the first occurrence of "to" and insert therefor -- in --.
Line 64, delete the second occurrence of "of" and insert therefor -- , --.

Column 28,
Line 1, delete "any one of".

Signed and Sealed this

Thirteenth Day of August, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.    : 6,267,957 B1
DATED         : July 31, 2001
INVENTOR(S)   : Howard Green et al.

It is certified that error appears in the above-identified patent and that said Letters Patent is hereby corrected as shown below:

<u>Title page,</u>
 Item [76], Inventors, please delete "Dijan" and insert therefor -- Djian --.

Signed and Sealed this

Eighth Day of April, 2003

JAMES E. ROGAN
*Director of the United States Patent and Trademark Office*